US00PP17373P3

(12) United States Plant Patent
Noack

(10) Patent No.: US PP17,373 P3
(45) Date of Patent: Jan. 23, 2007

(54) GROUND COVER ROSE PLANT NAMED 'NOA83100B'

(50) Latin Name: *Rosa hybrida*
Varietal Denomination: NOA83100B

(76) Inventor: Reinhard Noack, Im-Fenne 54, 33334 Gütersloh (DE)

( * ) Notice: Subject to any disclaimer, the term of this patent is extended or adjusted under 35 U.S.C. 154(b) by 0 days.

(21) Appl. No.: 11/043,095

(22) Filed: Jan. 27, 2005

(65) Prior Publication Data

US 2005/0183176 P1 Aug. 18, 2005

(30) Foreign Application Priority Data

Feb. 14, 2004 (DE) ..... ROS2407

(51) Int. Cl.
*A01H 5/00* (2006.01)

(52) U.S. Cl. ..... Plt./101

(58) Field of Classification Search ..... Plt./101
See application file for complete search history.

*Primary Examiner*—Anne Marie Grunberg
*Assistant Examiner*—Annette H Para
(74) *Attorney, Agent, or Firm*—Buchanan Ingersoll & Rooney PC

(57) ABSTRACT

A new and distinct variety for Ground Cover Rose plant is provided which forms on a substantially continuous basis sprays of attractive long-lasting bright red blossoms. The blossoms open on a reliable basis and retains their attractiveness upon aging. The new variety exhibits a compact spreading growth habit. The foliage is dark green and glossy and contrasts well with the bright red blossom coloration. The surfaces of leaves commonly are somewhat curled and partially closed. The blossom petals commonly detach cleanly upon full maturity. The plant propagates well from cuttings and by budding. Excellent resistance to Blackspot, Powdery Mildew, and Rust are displayed, and the plant is particularly well suited for growing as an attractive ornamental ground cover in the landscape.

2 Drawing Sheets

Figure 1:
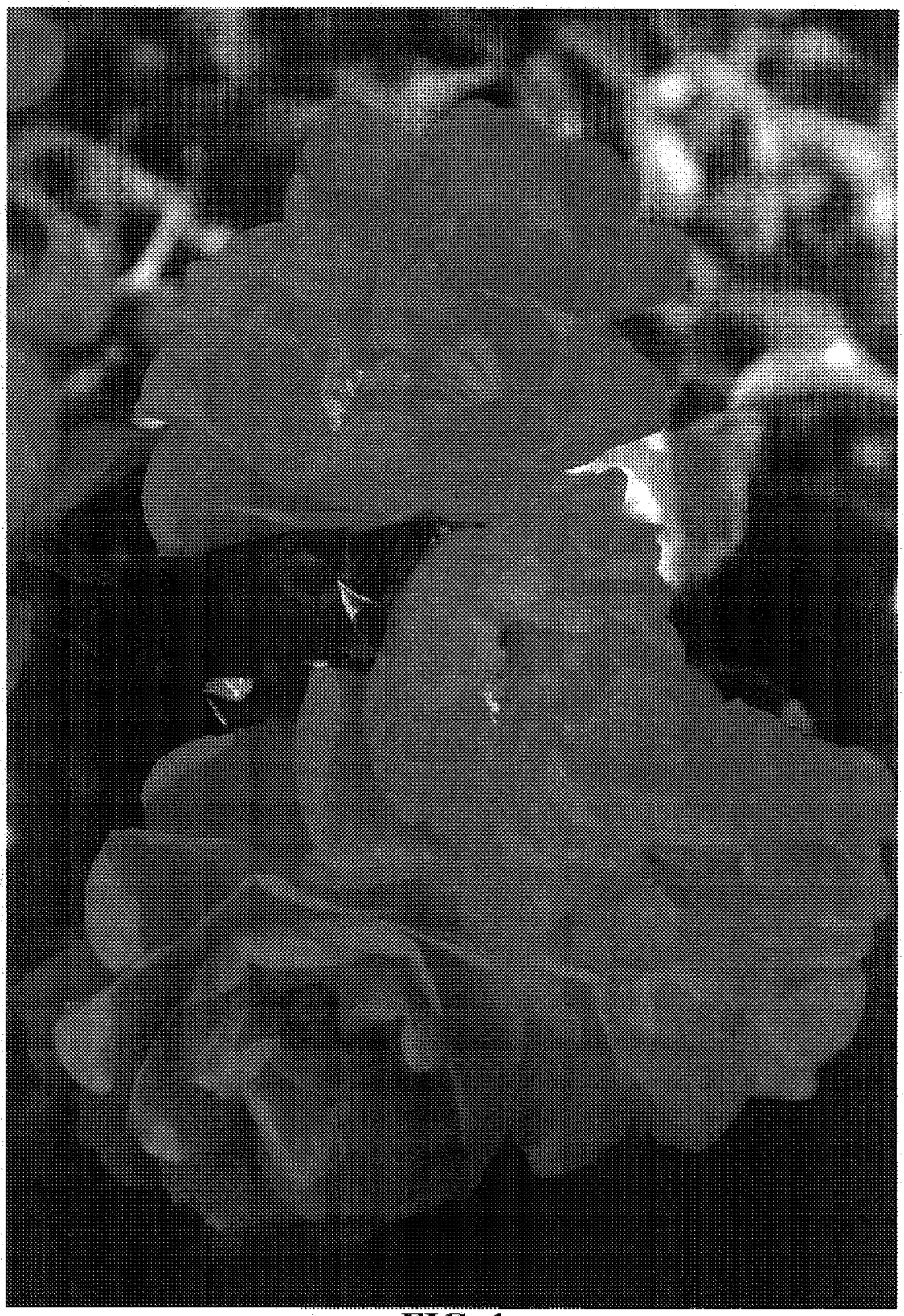

Botanical/commercial classification: *Rosa hybrida*/ Ground Cover Rose Plant.
Varietal denomination: cv. 'NOA83100B'.

SUMMARY OF THE INVENTION

Ground Cover rose plants are known and are being used to advantage in an increasing number of landscape plans and home gardens. However, there remains a need for additional varieties of Ground Cover roses with the demand being the greatest for those having highly attractive blossoms in combination with good disease resistance.

The new variety of *Rosa hybrida* Ground Cover rose plant of the present invention was created at Gütersloh, Germany, by artificial pollination wherein two parents were crossed which previously had been studied in the hope that they would contribute the desired characteristics. The female parent (i.e., the seed parent) was an unnamed and unreleased seedling (non-patented in the Untied States) maintained by Noack Rosen at Gütersloh, Germany. The male parent (i.e., the pollen parent) was 'Rotfassade' variety (non-patented in the United States). The parentage of the new variety can be summarized as follows:

Unnamed Seedling×'Rotfassade'.

The seeds resulting from the above pollination were sown and small plants were obtained which physically and biologically differ from each other. Selective study resulted in the identification of a single plant to the new variety.

It is found that the new variety of Ground Cover rose plant possesses the following combination of characteristics:

(a) forms in sprays attractive long-lasting bright red blossoms, (b) exhibits a dense compact and spreading growth habit, (c) forms attractive glossy dark green foliage that contrasts well with the bright red blossoms wherein the surfaces of the leaflets commonly are somewhat curled and partially closed, (d) exhibits exellent disease resistance with respect to Blackspot, Powdery Mildew, and Rust, and (e) is particularly well suited for growing as attractive ornamentation in the landscape.

The new variety meets the needs of the horticultural industry and can be grown to advantage as an attractive ornamental ground cover in parks, gardens, public areas, and residential landscapes.

The new variety of the present invention can be readily distinguished from its ancestors. More specifically, the unnamed female parent forms pale orange blossoms and smaller foliage, and the 'Rotfassade' male parent is a climber that forms large medium red blossoms.

The new variety of the present invention also can be readily distinguished from similar Ground Cover rose varieties upon an inspection of the flower coloration. For instance, the 'Korstesgli' variety (non-patented in the United States) forms blossoms that are R.H.S. Group No. 45D in cloration, and the 'Kortemma' variety (U.S. Plant Pat. No. 9,115) forms blossoms that are R.H.S. Group No. 45A in coloration.

The new variety of the present invention beginning in 2000 has been asexually reproduced by the rooting of cuttings, and by budding. Such asexual reproduction as performed in Gütersloh, Germany, has demonstrated that the characteristics of the new variety are firmly fixed and stable and are strictly transmissible from one generation to another. The new variety asexually reproduces in a true to type manner from one generation to another.

The new variety of the present invention has been named 'NOA83100B'.

BRIEF DESCRIPTION OF THE PHOTOGRAPHS

The accompanying photographs show as nearly true as it is reasonably possible to make the same, in color illustrations of this character, typical specimens of the new variety while growing outdoors. The illustrated rose plants were photographed during July, 2004, while growing in a field at Gütersloh, Germany. Such plants had been budded approximately one and one-half years earlier.

FIG. 1 illustrates a close view of the attractive bright red blossoms of the new variety.

Figure 2:
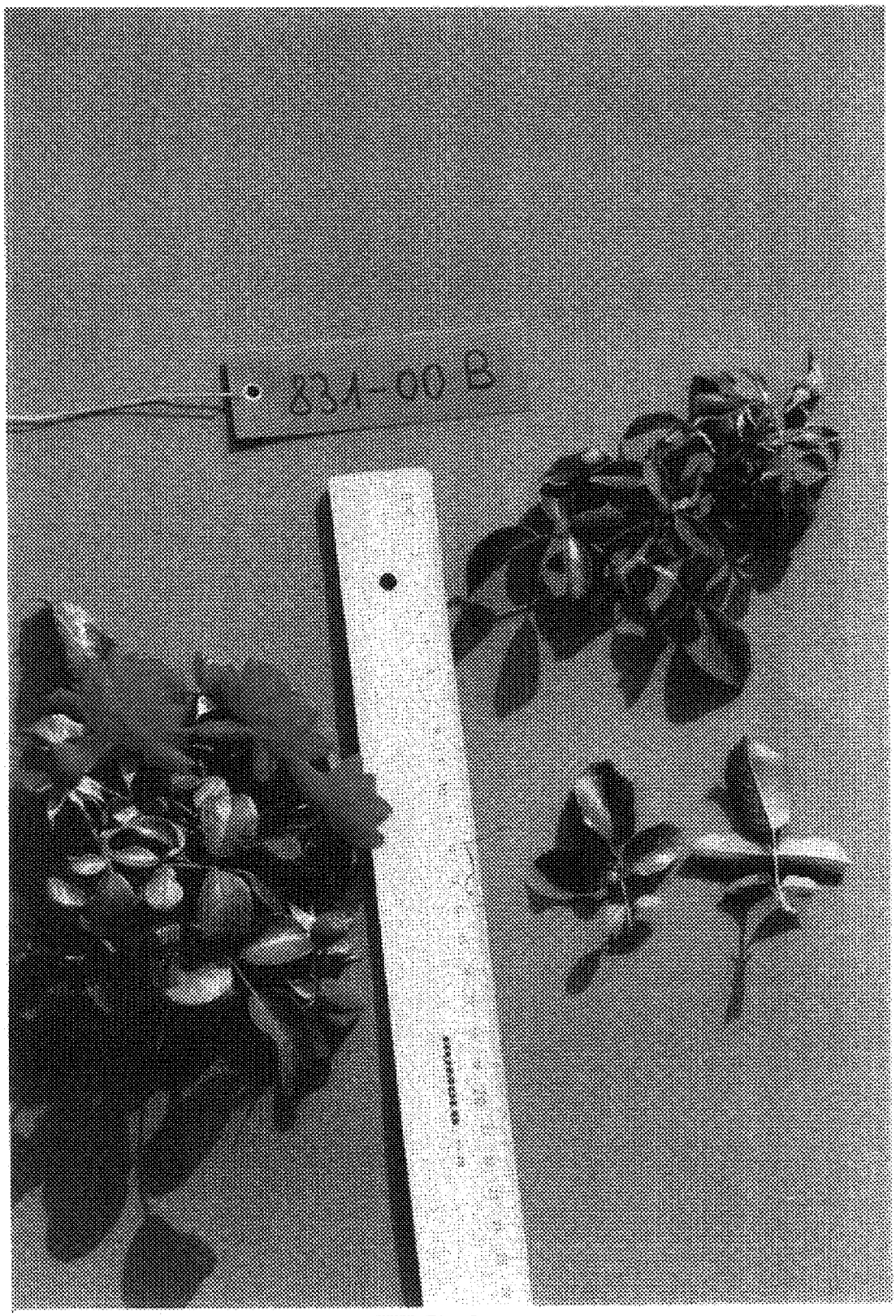

FIG. 2 illustrates at the right the upper and under surfaces of typical leaves and a cluster of foliage with a typical unopened bud, and at the left opening buds in various stages of opening, together with open blossoms and foliage wherein the glossy upper surface of the dark green leaflets is shown. The configuration of the somewhat curled and partially closed leaflets is illustrated. Dimensions in centimeters are included at the center.

DETAILED DESCRIPTION

The chart used in the identification of the colors is that of The Royal Horticultural Society (R.H.S. Colour Chart) of London, England. Color terminology in common terms sometimes is included as an aid to the reader. Such color terminology is to be accorded its customary dictionary significance. The description is based on the observation of typical specimens of the new variety while growing outdoors during July at Gütersloh, Germany.

Class: Ground Cover.

Plant:

*Form.*—Vigorous, young plants exhibit a dense compact growth habit, and with further maturity spread to form a compact bush with dense foliage that serves well as ground cover.

*Height.*—Approximately 60 cm on average.

*Width.*—Approximately 80 cm on average.

Branches:

*Color.*—Young stems: Green Group 139C with a smooth surface. Adult wood: Green Group 138B and darker green than the young stems and with a smooth surface.

*Thorns.*—Size: medium, aproximately 4.5 mm in length on average, slightly curved downward on the upper surface, and concave on the under surface. Position: irregular. Color: initially Green Group 138B when immature and changing to Greyed-Orange Group 172A at maturity. Quantity: typical for a Ground Cover rose plant.

Leaves:

*Stipules.*—Green in coloration.

*Leaflets.*—Number: commonly 5. Configuration: generally oval with a pointed apex, and commonly curled upwards at the margin thereby giving the leaves partially closed appearance. Quantity: very abundant. Size: medium. Serration: slightly serrate. Color: (young foliage): Upper surface: Green Group 138B. Under surface: Green Group 138B. Color: (adult foliage): Upper surface: Green Group 139B and glossy. Under surface: Green Group 139C and lighter green than the upper surface. General appearance: dense, dark green foliage that is glossy on the upper surface and matte on the under surface with the curled nature of the leaves being readily apparent. Texture: leathery. Stipules: green in coloration.

Inflorescence:

*Number of flowers.*—In clusters of flowers as a large spray.

*Peduncle.*—Soft green in coloration.

*Sepals.*—Shape: commonly do not extend much beyond the petals of the bud, pointed, and approximately 2 cm in length on average.

*Buds.*—Color when opening: strong bright red, Red Group 44A on the upper and lower surfaces.

*Flower.*—Form: somewhat flattened. Appearance: smooth on both petal surfaces. Diameter: approximately 5 cm on average. Color (when opening begins): Upper surface: predominantly Red Group 44A. Color (when blooming): Upper surface: predominantly Red Group 44A. The bright yellow coloration, Yellow Group 13A, of the pollen and the reproductive organs commonly is visible at the center. Under surface: predominantly Red Group 44A. Color (at the end of opening): Upper surface: bright red coloration, the Red Group 44A persists. Fragrance: none. Lasting quality: very good. Petal form: broad, fan-shaped, curved with a somewhat indented central area and margin areas that are slightly curved towards the center. Petal number: commonly approximately 16 on average. Petal arrangement: generally arranged in a regular pattern with overlapping edges. Petal drop: good with the petals detaching cleanly upon fully maturity. Stamens: regularly arranged around the styles. Filaments: Yellow-Orange Group 15A in coloration. Pollen: Yellow-Orange Group 15A in coloration. Stigmas: Yellow-Orange Group 15C in coloration. Styles: thin, regularly arranged at the center, tend to be substantially the same length, and Yellow-Orange Group 17B in coloration. Hips: generally oval to round, smooth in texture, approximately 1 cm in length, and initially green (Green Group 135C) in coloration changing to red (Red Group 42A) with maturity.

Development:

*Vegetation.*—Strong, compact, and vigorous.

*Blooming.*—Substantially continuous throughout the season in large sprays.

*Aptitude to bear fruit.*—Slight.

*Winter hardiness.*—Good.

*Resistance to diseases.*—Excellent with respect to Blackspot, Powdery Mildew, and Rust.

I claim:

1. A new and distinct Ground Cover Rose plant characterized by the following combination of characteristics:

(a) forms in sprays attractive long-lasting bright red blossoms, (b) exhibits a dense compact and spreading growth habit;

(c) forms attractive glossy dark green foliage that contrasts well with the bright red blossoms wherein the surfaces of the leaflets commonly are somewhat curled and partially closed, (c) exhibits excellent disease resistance with respect to Blackspot, Powdery Mildew, and Rust, and (d) is particularly well suited for growing as attractive ornamentation in the landscape;

substantially as illustrated and described.

* * * * *